(12) United States Patent
Zander et al.

(10) Patent No.: US 7,232,443 B2
(45) Date of Patent: Jun. 19, 2007

(54) LOCKING NAIL AND TARGETING APPARATUS

(75) Inventors: Nils Zander, Eckernförde (DE); Axel Cremer, Fahrenkrog (DE)

(73) Assignee: Stryker Trauma GmbH (DE)

( * ) Notice: Subject to any disclaimer, the term of this patent is extended or adjusted under 35 U.S.C. 154(b) by 261 days.

(21) Appl. No.: 10/391,896

(22) Filed: Mar. 19, 2003

(65) Prior Publication Data

US 2004/0010252 A1 Jan. 15, 2004

(30) Foreign Application Priority Data

Mar. 21, 2002 (DE) ............................ 202 04 655 U

(51) Int. Cl.
*A61B 17/58* (2006.01)

(52) U.S. Cl. ............................ 606/99; 606/62; 606/67; 606/98

(58) Field of Classification Search .................. 606/53, 606/54, 62, 64, 67, 86, 96, 97, 98, 99
See application file for complete search history.

(56) References Cited

U.S. PATENT DOCUMENTS

| 5,176,681 | A | | 1/1993 | Lawes et al. | |
| 5,334,192 | A | | 8/1994 | Behrens | |
| 5,352,227 | A | * | 10/1994 | O'Hara | 606/63 |
| 5,562,666 | A | | 10/1996 | Brumfield | |
| 5,620,445 | A | * | 4/1997 | Brosnahan et al. | 606/63 |
| 5,766,174 | A | | 6/1998 | Perry | |
| 5,766,179 | A | * | 6/1998 | Faccioli et al. | 606/98 |
| 5,855,579 | A | * | 1/1999 | James et al. | 606/62 |
| 6,039,739 | A | | 3/2000 | Simon | |
| 6,461,360 | B1 | * | 10/2002 | Adam | 606/67 |
| 6,629,976 | B1 | | 10/2003 | Gnos et al. | |

FOREIGN PATENT DOCUMENTS

| DE | 298 06 564 U1 | 9/1999 |
| DE | 299 80 004 U1 | 1/2001 |
| EP | 0 853 923 A1 | 7/1998 |
| EP | 1 095 626 A1 | 5/2001 |

* cited by examiner

*Primary Examiner*—David H. Willse
*Assistant Examiner*—Javier G. Blanco
(74) *Attorney, Agent, or Firm*—Lerner, David, Littenberg, Krumholz & Mentlik, LLP

(57) ABSTRACT

A locking nail for treating fractures of tubular bones has at least one cross-bore is provided at one end for the reception of a bone screw. The nail has a female thread at the end with the cross-bore for connection to a nail retention screw. The nail has an anti-rotation feature to anti-rotationally secure the rotational position of a joining sleeve which joins a targeting apparatus relative to the locking nail.

21 Claims, 4 Drawing Sheets

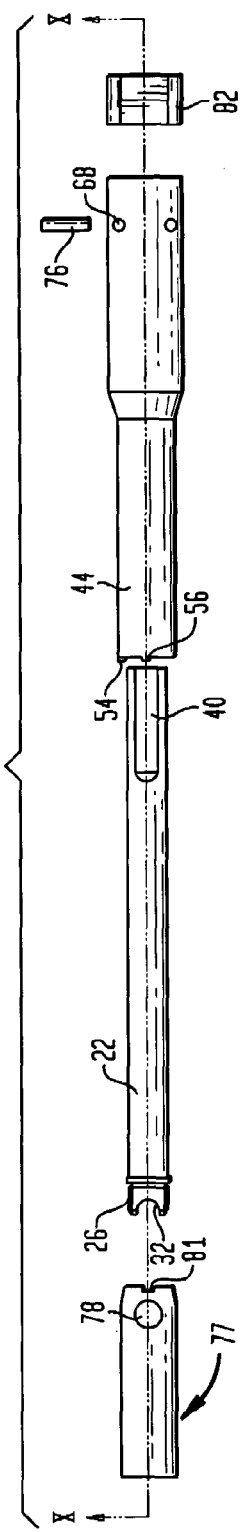
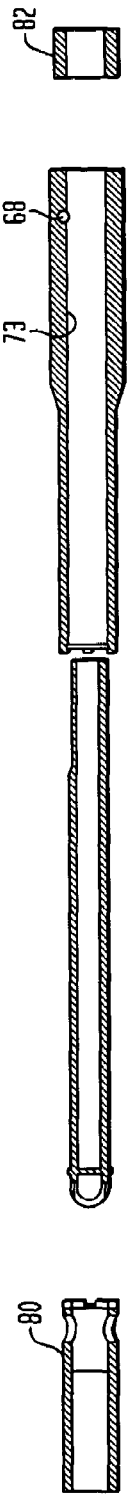
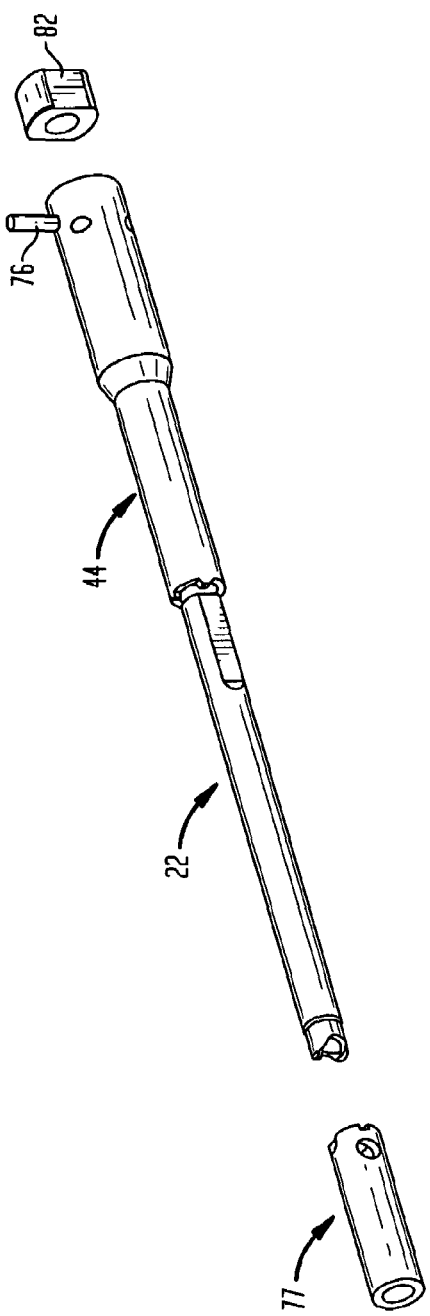
FIG. 9
FIG. 10
FIG. 11

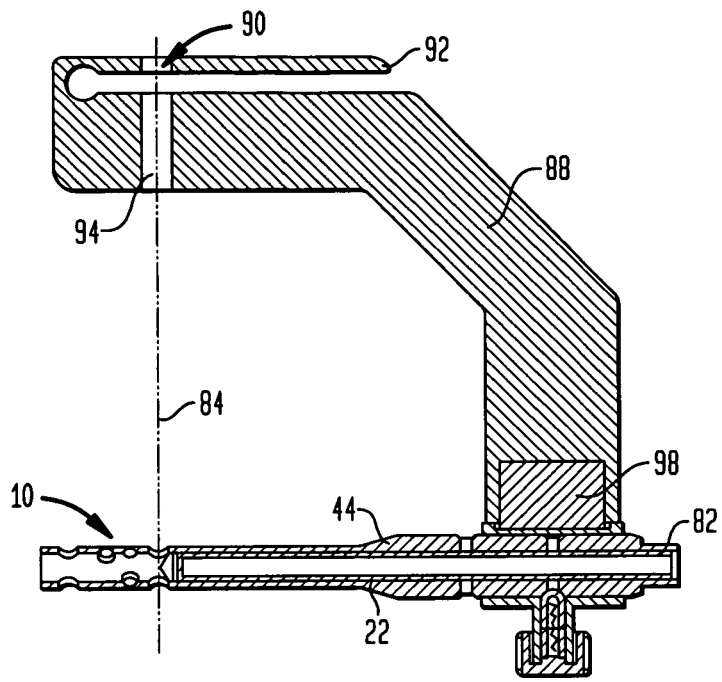
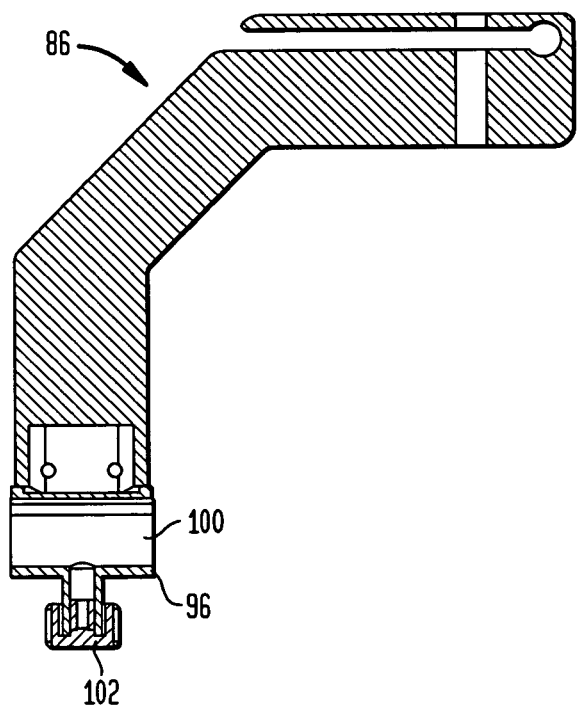
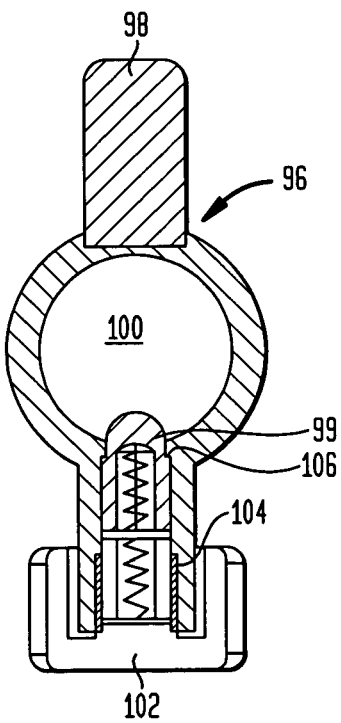

LOCKING NAIL AND TARGETING APPARATUS

BACKGROUND OF THE INVENTION

The present invention relates to a locking nail to treat fractures of tubular bones. The invention also relates to an aiming or targeting apparatus for a locking nail.

Locking nails for treating fractures of, for example, a femur, humerus and tibia, are known. It is common for locking nails to have cross-bores at the distal end and at least one cross-bore at the proximal end. Typically, bone screws are passed through the cross-bores which screws have been screwed into the corticalis at the opposite side of the bone. The bone screws secure the locking nail axially and rotationally. If supracondylar nails are used condylus screws may also be passed through the cross-bores.

A problem in employing locking nails, when inserted, is how to identify the position of the cross-bores to drill a hole into the corticalis in the proper place from outside. A number of aiming or targeting apparatus have become known, which work with X-rays to identify the position of the cross-bore relative to the targeting apparatus. Therefore, it is possible to drill a hole into the bone in the proper place by use of the targeting apparatus and a so-called drilling sleeve or aiming sleeve. In most cases, known targeting apparatus are firmly connected to the end of the nail used to drive in the nail. Thus, the position of the cross-bores may already be preset in an approximately precise way. However, it should be considered that the presumed position of the cross-bores will not coincide with the real one because of the curvature of the bone and the possible torsion the nail undergoes while it is driven in.

The disadvantage of using the targeting apparatus working with X-rays is that both the operator and patient are exposed to a radiation dose. Therefore, targeting apparatus are known that do not use radiography, but allow for the identification of the location of the cross-bore mechanically. Such are shown in U.S. Pat. Nos. 5,176,681, 5,334,192 and 6,039,739. Since it is necessary for the targeting apparatus to be connected to the locking nail it has hitherto been impossible to identify the location of cross-bores and to introduce bone screws for those positioned close to the nail end. This is why cross-bores always need to be at a minimum distance from the end of the locking nail.

SUMMARY OF THE INVENTION

It is the object of the invention to provide a locking nail and a targeting apparatus which, using a simple method to make it possible to safely identify cross-bores close to the end of the locking nail and to introduce bone screws or condylus screws therein.

The locking nail of the present invention is provided, at one of its ends, with at least one cross-bore for the reception of a screw, particularly a condylus screw or a bone screw. The end with the cross-bore is provided with a female thread which serves for connection to a nail retention screw. The locking nail is further designed to locate the rotational position of a joining sleeve or adaptor of a targeting apparatus relative to the locking nail. The cross-bore located most closely to the end of the locking nail may be at a small distance from the nail end. The nail retention screw of the targeting apparatus is threaded onto the locking nail in an axial direction. The radial location of the targeting apparatus is performed via a joining sleeve of the targeting apparatus, which, when loaded on the nail retention screw, is located in the required rotational orientation, relative to the locking nail. Thus, the inventive locking nail is configured such as to locate the targeting apparatus axially and rotationally independently of each other. To this end, it is sufficient to provide a small distance between the end of the locking nail and the cross-bore.

To locate the rotational position of the joining sleeve or adaptor relative to the locking nail, the end of the locking nail adjacent the at least one cross-bore preferably has one or more recesses and/or projections on its face. In the preferred embodiment three recesses be provided on the face in which adjacent recesses enclose an angle of about 90° or 180° with each other. Thus, the third recess is spaced at 90° to the middle of the three recesses and thus 180° from the first recess. If only two recesses are provided they would be at 90° from each other. The effect of recesses disposed in this way is that a joining sleeve or adaptor having corresponding projections may engage the recesses only in exactly one position. Any other arrangement of projections and recesses that locate the joining sleeve in a distinct position relative to the locking nail is feasible as well. Also, it is possible to locate the joining sleeve in a position and in its other position turned through 180°.

According to the invention, the object is also attained by having a targeting apparatus which couples to the adaptor or sleeve. The targeting apparatus has a nail retention screw which engages the joining sleeve. The nail retention screw, at its ends facing the locking nail, is provided with two extensions which project in an axial direction. The space or recess between the extensions, when in a predetermined position, opens a cross-bore in the locking nail. In the inventive targeting apparatus, the nail retention screw is introduced into the nail bore to an extent such as to close the cross-bore disposed closest to the end of the nail by the nail retention screw extensions, but is left open by orienting the space between the extensions parallel to the cross-bore. At the other end, the nail retention screw also has a bearing surface extending in an axial direction. The joining sleeve or adaptor is further provided with key and recess to anti-rotationally secure the joining sleeve with respect to the locking nail in the predetermined position of the nail retention screw. In the targeting apparatus of the present invention, the joining sleeve is secured from rotation with respect to the locking nail. If the joining sleeve or adaptor is brought to the anti-rotationally secured position the nail retention screw is automatically brought to its predetermined position in which the extensions open the cross-bore.

Preferably, the extensions of the nail retention screw are provided with a thread on the outside. The bottom between the extensions is rounded and the free ends of the extensions are rounded. The nail retention screw is fixed by threading to the end of the locking nail adjacent the at least one cross-bore with the space between the extensions aligned with the cross-bore. The extensions are shaped such that a Kirschner wire introduced through the extensions after drilling may remain in the bore if the nail retention screw is removed, and is merely urged to the edge thereof is the screw rotates.

Preferably, the nail retention screw has a circumferential projection at the end facing the locking nail. A circumferential groove is provided between the portion having the extensions and the projection. The joining sleeve has three recesses adjacent ones of which enclose an angle of about 90° or 180° with each other on the face and, in the inserted position, engage the recesses on the locking nail.

The bearing surface of the nail retention screw is preferably formed as a flattened area or groove. However, it is also possible to provide the shank of the nail retention screw with a plurality of flat surfaces in a region.

It is preferred that a bore in the sleeve wall and a pin inserted therein are provided as a driver for the central bore in the joining sleeve. The pin inserted in the bore extends perpendicularly and at a distance from a central longitudinal axis of the joining sleeve. The two ends of the pin are held in place in the wall of the joining sleeve. The joining sleeve or adaptor further is provided with orientation recesses for a handle portion of the targeting apparatus. The handle portion is preferably provided with spring detent for location of the handle axially and rotationally of relative to the orientation recesses on the sleeve. To this end, the handle portion preferably has a bore into which a spring-biased stud projects for engaging one of the orientation recesses on the joining sleeve.

The handle portion further is provided with an arresting or locking screw which, when in a threaded-in position, presses and locks the stud against the orientation recess of the joining sleeve or adaptor.

For location in the joining sleeve in an axial direction, the nail retention screw, at its end facing away from the locking nail, is provided with a threaded portion which projects beyond the end of the joining sleeve when it is in its fully inserted position. To locate the joining sleeve in an axial direction, a nut which presses the joining sleeve against the locking nail is screwed onto the threaded portion of the nail retention screw.

BRIEF DESCRIPTION OF THE DRAWINGS

The present invention will be described in more detail below with reference to an embodiment. In the drawings:

FIG. 9 shows an exploded view of the nail retention screw and joining sleeve;
FIG. 10 shows a section along line 10—10 of FIG. 9;
FIG. 11 shows an exploded view of the nail retention screw and joining sleeve in a perspective view;
FIG. 12 shows a sectional representation of the targeting apparatus placed on top of the locking nail;
FIG. 13 shows a handle member of the targeting apparatus of FIG. 12;
and
FIG. 14 shows a handle member mounting on the joining sleeve.

DETAILED DESCRIPTION

Figure 1:
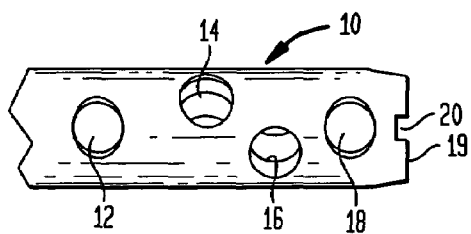
FIG. 1 shows the distal end of a locking nail.

FIG. 1 shows the distal end of a locking or supracondylar nail 10. The locking nail is provided with four cross-bores 12, 14, 16 and 18 which serve for receiving bone screws and/or condylus screws to locate the locking nail both axially and radially in the bone. On the end face 19, locking nail 10 is provided with two recesses 20 the nearest one of which is shown and the second being spaced around the nail from the other at an angle of 180° in FIG. 1. In the preferred embodiment, recess 20 is of a rectangular shape. In the locking nail illustrated, the cross-bore 18 is at a distance of 6 mm from the free end of the nail. Not shown in FIG. 1 is a female thread which is provided inside the locking nail and which from the end 19 of the locking nail extends beyond the beginning of the cross-bore 18.

Figure 2:
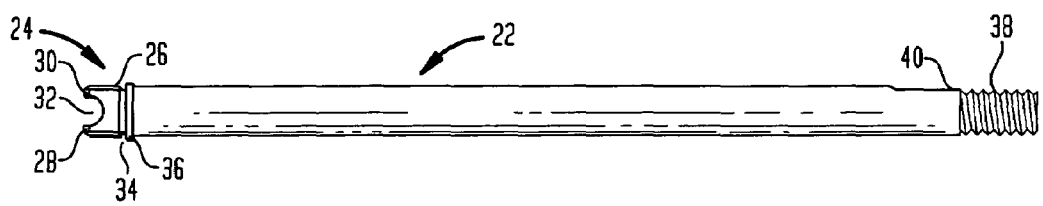
FIG. 2 shows a nail retention screw in a first side view.

FIG. 2 shows a nail retention screw 22. The end 24 is provided for connection to locking nail 10. End 24 has a male thread 26 which corresponds to the abovementioned female thread of locking nail 10. The end 24 has two extensions 28 and 30 which define a recess 32 therebetween. Extensions 28, 30 project in axial direction and form a U-shaped end of the nail retention screw. A circumferential groove 34 is provided which adjoins the threaded portion and is followed by a circumferential projection 36.

Figure 3:
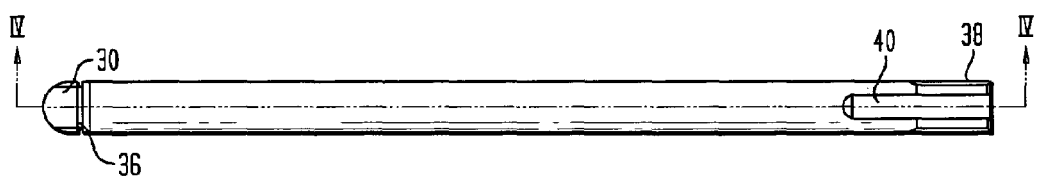
FIG. 3 shows a nail retention screw of FIG. 2 in a second side view.
Figure 4:
FIG. 4 shows a section along line 4—4 of FIG. 3.
Figure 5:
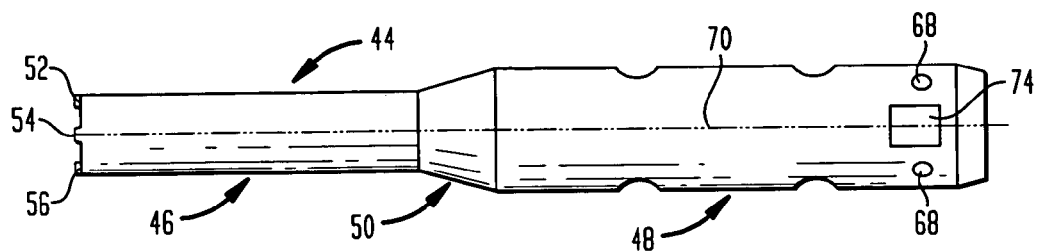
FIG. 5 shows a joining sleeve as seen from a first side view.

The opposite end of nail retention screw 22 is provided with a threaded portion 38. The thread 38 is interrupted in the area of the flattened portion 40. Hence, the thread 38 also includes a part threaded portion. FIG. 3 shows a plan view of the flattened portion 40. A section along line 4—4 of FIG. 3 is illustrated in FIG. 4. The sectional representation 4 makes it apparent that the region 24 is separated by a partition or wall 42 from the shank of the nail retention screw.

The joining sleeve or adaptor of the present invention will now be described in greater detail with reference to FIGS. 5 through 8. The joining sleeve 44 has a cylindrical shank with a first portion 46 and a second portion 48 which has a larger radius than that of first portion 46. In the preferred embodiment, the transition area 50 between the first and second portions has a conical configuration. The inner diameter of an internal bore of the joining sleeve matches the outer diameter of the nail retention screw so that sleeve 44 may be slid onto nail retention screw 22.

The end of the first portion 46 is provided with three projections 52, 54 and 56. The projections 52 through 56 correspond with recesses 20 in the locking nail. The projections 52, 54 and 56 are arranged in a semicircular segment so that projections 52 and 54 enclose an angle of 90°, projections 54 and 56 also enclose an angle of 90°, and projections 56 and 52 enclose an angle of 180°.

The outer surface of second portion 48 has provided therein location elements or orientation recesses 58, 60 and 62. Each orientation recess has a funnel-shaped area 64 with a central through bore 66.

A through bore 68 is provided in the wall at the end of the second portion 48. The through bore 68 is spaced from the central longitudinal axis 70 of the sleeve by the distance 72 and extends perpendicularly to axis 70. As shown in FIG. 10, a pin 76 is pressed into the through bore 68 and intersects the inner bore 73 of sleeve 44 and reduces the diameter thereof. The cross-section of sleeve bore 73 with pin 68 inserted corresponds to flattened portion 40 of nail retention screw 22.

Figure 6:
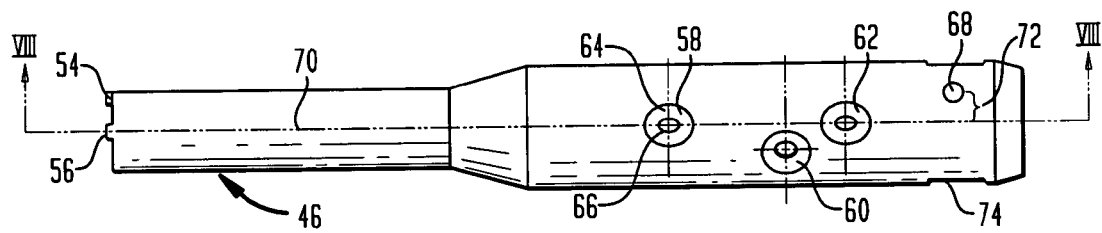
FIG. 6 shows a joining sleeve of FIG. 5 as seen from a second side view.
Figure 7:
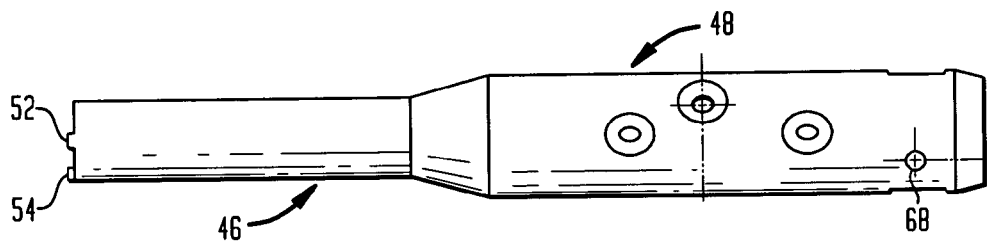
FIG. 7 shows a joining sleeve of FIG. 5 as seen from a third side view.
Figure 8:
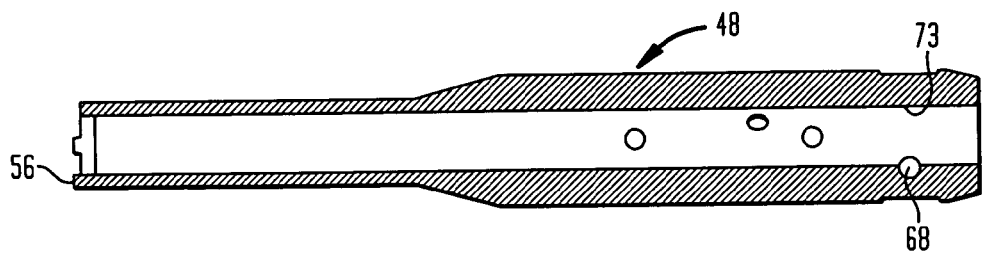
FIG. 8 shows a section along line 8—8 of FIG. 5.

As shown in FIGS. 6 and 7, the second portion 48 also has provided therein wrench-engaging surfaces 74 for an open-ended wrench or the like.

FIG. 9 shows an end of a locking nail 77 having a cross-bore 78. The end of the locking nail is provided with a female thread 80 as can be seen from the sectional representation of FIG. 10. Also provided are recess 81 which are similar to recess 20 of FIG. 1 but oriented at 90° on end 77. The nail retention screw 22 is screwed into the end of locking nail 77 by means of its male thread 26. Pin 76 is pressed into bore 68 of joining sleeve 44. As described above, pin 76 reduces the inner bore 73 diameter of the sleeve 44 as can be seen from FIG. 10. If joining sleeve or adaptor 44 with the pin 76 pressed in a bore 68 is slid onto nail retention screw 22 it can only be slid on if the pin 76 bears on the flattened portion 40. Retention sleeve 44 thus assembled on screw 20 is appropriately oriented by the projections 54 and 56 engaging the recesses 81 on the end of the locking nail. Each recess 81 corresponds to a projection 54 and 56 here. The interaction between the projection and the recess allows the joining sleeve and, hence, the nail retention screw to be located only in a single position on the locking nail. In this position, the recess 32 nail retention screw 22 is aligned with cross-bore 78 so that the bore is open.

Joining sleeve or adaptor 44 is secured by a nut 82 which is screwed onto the threaded portion 38 of the nail retention screw to axially lock the screw 22 within sleeve 44.

FIG. 12 shows a cross-section through the whole targeting apparatus in its assembled position. Locking nail 10 has screwed thereon, on end 19, the nail retention screw 22 on top of which joining sleeve 44 is located. Joining sleeve 44 is secured on screw 22 by the nut 82. The extension 28, 30 of nail retention screw 22 are oriented in such a way that the cross-bore located closest to the end is open and aligned along the imaginary line 84. The second portion 48 of joining sleeve 44 has coupled to the outer circumference thereof a handle member 86 of the targeting apparatus. The handle member 86 is secured both axially and rotationally on sleeve 44. The handle member 86 has a first portion 88 which, in the preferred embodiment, is configured to be grasped and has a targeting bore 90 for receiving an aiming or drilling sleeve. The cantilevered part 92, when pressed down, secures a sleeve inserted in the aiming bore 94 in its inserted position. Such a system is shown in U.S. Pat. No. 6,039,739.

Referring to FIGS. 13 and 14, first portion 88 is connected to a tubular locating device 96 via any convenient method. In the preferred embodiment, the locating device 96 has a tongue 98 via which fits in to a recess in the handle member for this connection. The locating device 96 has a central bore 100 the inner diameter of which corresponds to the outer diameter of the sleeve 44 in at second portion 48. A spring-biased stud 99 extends into the bore 100 and has a rounded tip extending into the bore 100 and cooperates with the funnel-shaped indentations of the location elements or orientation recesses 58, 60 and 62 to form a snap connection. The stud 98 snaps into one of the marking recesses 58, 60 and 62 on the joining sleeve 44. If the stud 99 has not snapped into a marking recess it will be pressed outwardly against the spring tension and the locating element 96 may be moved axially and rotationally on the joining sleeve.

The stud 99 which is snapped in is secured via a locking screw 102. Locking screw 102 has a shank 104 which is screwed into the bore of the stud 99 via a thread. When in its screwed-in position, the shank 104 bears on the stud 99, pressing it against joining sleeve 44.

A circumferential step 106, which cooperates with a circumferential projection of the locating device 96, secures the stud 99 and prevents it from being pushed too far into the opening 100.

To allow for a better orientation of the device, individual marking recesses 58, 60 and 62 may be labeled to make it evident to which of the cross-bores the targeting bore 90 is directed. After the targeting device 86 is oriented the locking screw 102 secures it in position. Thus, for example, when position in recess 60 opening 94 is aligned with cross-bore 16 of nail 10. When positioned in recess 62 it is aligned with cross bore 18 etc.

An insertion of a condylus or locking screw into the cross-bore disposed closest to the border is effected by means of a Kirschner wire which, for example, is 1.8 mm in diameter. After a hole is drilled, e.g. by means of a drill preferably 5 mm in diameter, the Kirschner wire is introduced, allowing the targeting apparatus to be removed. If the condylus screw were inserted prior to the removal of the targeting apparatus nail retention screw 22 could no longer be unscrewed from the locking nail because the extensions 28, 30 thereof are blocked by the condylus screw. However, the extensions are rounded to such an extend that the Kirschner wire is forced aside in the cross-bore, thus allowing the nail retention screw to be unscrewed with the wire in place. Subsequently, the condylus screw is introduced into the cross-bore via the Kirschner wire and is screwed in place.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A targeting apparatus for connection to a locking nail having a threaded end with at least one crossbore adjacent thereto comprising:
   a nail retention screw having an end intended for insertion into and attachment to the threaded end of the locking nail, the retention screw end having a recess formed between two axial projections which recess, when in a predetermined position, leaves open the cross-bore in the locking nail;
   an adaptor in the form of a joining sleeve which has a drive element which, when the sleeve is inserted onto the nail retention screw, engages the nail retention screw such as to cause the nail retention screw to rotate together with the joining sleeve, said sleeve has means to anti-rotationally secure the joining sleeve with respect to the locking nail in the predetermined position of the nail retention screw; and
   an aiming device including a targeting bore rotatably mounted on the adaptor for targeting the cross-bores in the locking nail.

2. The targeting apparatus as set forth in claim 1 wherein the end of the nail retention screw for engaging the locking nail has an outer thread for connection to a female thread on the locking nail.

3. The targeting apparatus as set forth in claim 2 wherein the recess is rounded.

4. The targeting apparatus as set forth in claim 3 wherein the projections have free ends which are rounded.

5. The targeting apparatus as set forth in claim 4, wherein the nail retention screw has a circumferential projection and an extension adjacent the end facing the locking nail.

6. The targeting apparatus as set forth in claim 5 wherein a circumferential groove is provided between the extension and the circumferential projection.

7. The targeting apparatus as set forth in claim 6 wherein the joining sleeve has three projections or recesses on the face adjacent the locking nail which enclose an angle of about 90° or 180° with each other.

8. The targeting apparatus as set forth in claim 6 wherein the joining sleeve has projections.

9. The targeting apparatus as set forth in claim 8 wherein the drive element of the joining sleeve is a bore therein for receiving the retention screw and a pin adapted for insertion in the bore.

10. The targeting apparatus as set forth in claim 9 wherein the bore extends at a distance from a central longitudinal axis of the joining sleeve and the pin intersects a bearing surface.

11. The targeting apparatus as set forth in claim 10 wherein the joining sleeve has orientation recesses for a handle portion.

12. The targeting apparatus as set forth in claim 11 wherein the handle portion has a means for location on the sleeve axially and rotationally relative to the orientation recesses.

13. The targeting apparatus as set forth in claim 12 wherein the handle portion has a bore for receiving the joining sleeve into which a spring-biased stud projects for engaging one of the orientation recesses.

14. The targeting apparatus as set forth in claim 13 wherein the handle portion has a locking screw which, when in a threaded-in first position, presses the stud into one of the orientation recesses.

15. The targeting apparatus as set forth in claim 14 wherein the nail retention screw, at an end facing away from the locking nail, has a threaded portion which projects from the joining sleeve when it is in a fully inserted position.

16. A targeting device for a locking nail implanted in a bone, the locking nail having at least two axially spaced cross-bores circumferentially offset from one another, comprising:
    an adaptor for selective assembly to and disassembly from the locking nail, the adaptor having a coupling means at one end thereof for coupling the adaptor to a first end of the locking nail in a desired rotational position, the coupling means having rotational location elements for engaging rotational location elements on the locking nail to set the desired rotational position, the adaptor having at least two cross-bore location elements thereon each at a location on the adaptor corresponding to the axial and circumferential location of one of the locking nail cross-bores when the adaptor is aligned at said desired rotational position; and
    a targeting arm including guides alignable with the locking nail cross-bores for directing a drill into the bone adjacent the cross-bores, said targeting arm having a mounting portion for engaging said adaptor for axial and rotational movement thereon, said mounting portion having a releasable cross-bore locking element for selectively locking the targeting arm in a position corresponding to one of said cross-bore location elements on the adaptor.

17. The targeting device as set forth in claim 16 wherein the adaptor is in the form of a sleeve with an internal bore.

18. The targeting device as set forth in claim 17 wherein said coupling means includes a retention screw extending through said bore in said sleeve and having a first end threadably engaged with said one end of said locking nail.

19. The targeting device as set forth in claim 18 wherein said retention screw is coupled to said sleeve for rotation therewith.

20. The targeting device as set forth in claim 19 wherein said sleeve coupling means includes a key element at said one end thereof engageable with a key element on said first end of said locking nail for setting said desired rotational position.

21. The targeting device as set forth in claim 20 wherein said retention screw has a recess in said first end thereof alignable with a cross-bore in the locking nail.

* * * * *

UNITED STATES PATENT AND TRADEMARK OFFICE
CERTIFICATE OF CORRECTION

PATENT NO. : 7,232,443 B2 Page 1 of 1
APPLICATION NO. : 10/391896
DATED : June 19, 2007
INVENTOR(S) : Nils Zander and Axel Bernhard Cremer It is certified that error appears in the above-identified patent and that said Letters Patent is hereby corrected as shown below:

Cover page, item [57] under ABSTRACT, line 2, "cross-bore is provided" should read --cross-bore provided--.
Column 1, line 16, "used condylus" should read --used, condylus--.
Column 1, line 50, "which, using" should read --which use--.
Column 2, line 11, "recesses be provided" should read --recesses are provided--.
Column 2, line 57, "thereof is the" should read --thereof as the--.
Column 3, line 11, "with spring detent" should read --with a spring detent--.
Column 3, line 65, "20 the nearest" should read --20, the nearest--.
Column 5, line 2, "screw 22 it" should read --screw 22; it--.
Column 5, line 10, "recess 32 nail" should read --recess 32 of nail--.
Column 5, line 20, "extension" should read --extensions--.
Column 5, line 40, "in at second" should read --in second--.
Column 5, line 45, "stud 98" should read --stud 99--.
Column 5, line 63, "oriented the locking" should read --oriented, the locking--.
Column 6, line 8, "apparatus nail" should read --apparatus, nail--.
Column 6, line 29, "crossbore" should read --cross-bore--.

Signed and Sealed this

Fifteenth Day of July, 2008

JON W. DUDAS
*Director of the United States Patent and Trademark Office*